United States Patent [19]

Ullrich et al.

[11] Patent Number: 5,317,015
[45] Date of Patent: May 31, 1994

[54] AZACYCLIC BISPHOSPHONATES AS ANTICHOLESTEROLEMIC AGENTS

[75] Inventors: John W. Ullrich, Philadelphia, Pa.; Raymond D. Youssefyeh, Princeton Junction, N.J.; Daniel L. Cheney, Audubon; Christopher J. Burns, Bryn Mawr, both of Pa.

[73] Assignee: Rhone-Poulenc Rorer Pharmaceuticals Inc., Collegeville, Pa.

[21] Appl. No.: 877,574

[22] Filed: May 1, 1992

[51] Int. Cl.$^5$ .................... A61K 31/675; A61K 31/66
[52] U.S. Cl. ........................................ 514/79; 514/80; 514/89; 514/102; 514/107; 514/824
[58] Field of Search ................ 514/79, 80, 82, 89, 514/91, 102, 107, 824

[56] References Cited

U.S. PATENT DOCUMENTS

| | | | |
|---|---|---|---|
| 4,416,877 | 11/1983 | Bentzen et al. | 514/107 |
| 5,130,304 | 7/1992 | Binderup et al. | 514/91 |
| 5,157,027 | 10/1992 | Biller et al. | 514/107 |

*Primary Examiner*—Frederick E. Waddell
*Assistant Examiner*—Kimberly R. Jordan
*Attorney, Agent, or Firm*—James A. Nicholson; Martin F. Savitzky; Raymond S. Parker, III

[57] ABSTRACT

This invention relates to a method of lowering abnormally high serum cholesterol levels in the body without significantly reducing mevalonic metabolite synthesis and to novel pharmacological compositions containing as an active ingredient bisphosphonic acid and ester compounds containing a mono-, bi- or tricyclic ring linked with a bisphosphonate moiety through a basic amino alkylene group. This invention also provides novel bisphosphonate compounds and the processes for their preparation.

9 Claims, No Drawings

AZACYCLIC BISPHOSPHONATES AS ANTICHOLESTEROLEMIC AGENTS

FIELD OF THE INVENTION

The present invention relates to the treatment of diseases associated with undesirable cholesterol levels in the body, and particularly of diseases of the cardiovascular system, such as atherosclerosis.by the administration of a novel phosphorus containing compound.

Only about 7% of the total body cholesterol circulates in the plasma, where it has been linked to atherosclerosis. The remaining 93% is located in cells, where it performs vital structural and metabolic functions. Although all animal cells require cholesterol, they face a complex problem in·regulating the amount of intracellular cholesterol present. Under normal conditions, cholesterol can be synthesized endogenously or it can be obtained exogenously by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake. Increased LDL uptake by cells, especially liver cells, has been shown to lower plasma cholesterol levels.

LDL binds to specific receptors found on the surfaces of the cells and is internalized by receptor-mediated endocytosis. Inside the cell, the cholesterol ester component is hydrolyzed by lysosomal enzymes to liberate free cholesterol. The free cholesterol has the following four important regulatory actions on the cell's cholesterol metabolism:

(1) Suppression of cholesterol biosynthesis by downregulation of the rate limiting enzyme, HMG-CoA reductase;
(2) Suppression of the synthesis of LDL receptors;
(3) Activation of the ACAT enzyme, which catalyzes the formation of cholesterol esters for storage; and
(4) Suppression of squalene synthetase activity.

The first three regulatory actions are taken to prevent an overaccumulation of free cholesterol in the cell. Suppression of squalene synthetase activity by free cholesterol, the fourth response above, occurs only after the HMG-CoA reductase enzyme has been supressed by more than 90%, which, accordingly, reduces the synthesis of mevalonic acid and all of its metabolites. Farnesyl pyrophosphate (FPP), is an important mevalonate metabolite, located at the branch point of the mevalonate pathway. It is the immediate precursor of squalene, whose sole fate is cholesterol synthesis, as well as of some vital nonsterol products (e.g. dolichol, ubiquinone, and the farnesylated proteins), which are essential for cell growth. Cholesterol is required in much larger amounts than the nonsterol products and in the absence of LDL supplied cholesterol, the vast bulk of farnesyl pyrophosphate is used to produce cholesterol by way of squalene. However, when free cholesterol is present and HMG-CoA reductase has been suppressed, squalene synthetase is also suppressed in order to divert farnesyl pyrophosphate from the sterol pathway, into the crucial nonsterol pathways. It should be pointed out that even though squalene synthetase is suppressed about 90% by free cholesterol, the enzyme is still present in large excess in the cell. Thus suppression of squalene synthetase does not influence the rate of cholesterol biosynthesis. Rather its purpose is to support the synthesis of the nonsterol products by maintaining adequate concentrations of farnesyl pyrophosphate. This is important at a time when the synthesis of farnesyl pyrophosphate has been greatly reduced.

Treatment with an HMG-CoA reductase inhibitor blocks the production of mevalonic acid and thus inhibits the biosynthesis of cholesterol. But unlike the normal physiological regulation of the mevalonate pathway, there is no concurrent suppression of the squalene synthetase enzyme. The small amounts of farnesyl pyrophosphate still being produced still follow the sterol pathway. The intracellular concentration of farnesyl pyrophosphate drops to levels so low that the farnesylated proteins prepared therefrom can no longer be synthesized. It should be noted that farnesylated proteins are involved in feedback supression regulation of HMG CoA reductase, and, accordingly, the loss of this feedback regulation results in a 5- to 10-fold increase in the amount of the HMG-CoA reductase enzyme present in the cell. The increased amount of enzyme can also be inhibited by the HMG CoA reductase inhibitor, but at a higher dose than would have been necessary had the amount of the HMG-CoA reductase enzyme remained the same.

Since HMG CoA reductase is a rate-limiting enzyme in cholesterol biosynthesis, inhibitors of HMG CoA reductase are potent hypocholesterolemic agents in humans. Although these inhibitors are relatively safe, side effects like hepatotoxicity and myopathy have been observed. Inhibition of squalene synthetase will not result in reduction of vital mevalonate metabolites and thus a squalene synthetase inhibitor may offer the advantage of fewer side effects compared to that observed with inhibitors of HMG CoA reductase. It may also result in feed-back inhibition of HMG CoA and thus become a more useful hypocholesterolemic agent.

REPORTED DEVELOPMENTS

The literature describes the cholesterol biosynthetic pathway and possible means for the inhibition of squalene synthetase. In a series of papers including *J. Am. Chem. Soc.*, 1982, 104, 7376–7378 and *J. Am. Chem. Soc.*, 1989, 111, 3734–3739, C. Dale Poulter, et al disclose that ammonium substituted cyclopropyl polyene compounds mimic the topological and electrostatic properties of the primary cation and tertiary cation of presqualene pyrophosphate and in the presence of phosphate buffer, inhibit squalene synthetase. Scott A. Biller et al in *J. Med. Chem.*, 1988, 31, 1869–1871 disclose that a series of stable, non-ionizable analogues of farnesyl pyrophosphate, comprising phosphomethylene phosphate polyene compounds, inhibit squalene synthetase.

Poulter, et al. in *J. Am. Chem. Soc.*, 1987, 109, 5542, also describes the compounds having the structure

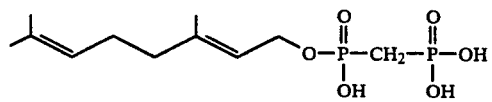

which he evaluated as an alternative substrate for avian liver farnesyl diphosphate and lemon peel cyclose. In *J. Am. Chem. Soc.*, 1987, 109, 5544, R. W. McClard and C. D. Poulter reported that phosphinylphosphonates of the structure

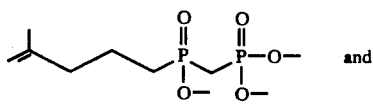

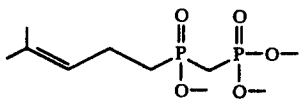

were competitive inhibitors of the 1,4-condensation between isopentenyl diphosphate and geranyl diphosphate. They also reported the isolation of farnesyl phosphinylphosphonate

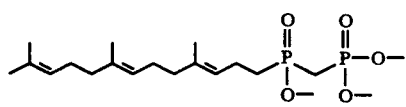

which could be a potential inhibitor of squalene synthetase.

The present invention relates to a class of novel substituted bisphosphonic acid and ester derivative compounds which exhibit squalene synthetase inhibition properties for use in a method of lowering or maintaining lowered serum cholesterol in humans and other mammals.

SUMMARY OF THE INVENTION

In accordance with the present invention, compounds exhibiting properties which reduce levels of serum cholesterol in the body without significantly reducing mevalonic metabolite synthesis are used as therapeutic agents, and are likely to exhibit fewer side effects than agents which act by inhibiting the HMG-CoA reductase enzyme. This invention provides a method for lowering serum cholesterol levels and maintaining lowered serum cholesterol levels, and pharmaceutical compositions containing as an active ingredient bisphosphonic acid and ester compounds containing a mono-, bi- or tricyclic ring linked with a bisphosphonate moiety through a basic amino alkylene group.

More specifically, the compounds of this invention are described by Formula I below.

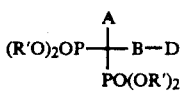

where:

A is hydrogen, hydroxy, alkoxy, amino or mono- or di-alkyl amino;

B is $(CR_1R_2)_m$, $CR_1{=}CR_1$, $CR_1{=}CR_1CR_1R_2$ or $CR_1R_2CR_1{=}CR_1$ where m is 1-3;

D is Z, —NR—X or —NR—$(CH_2)_{1\text{-}2}$—Z;

X is

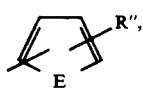

where E is $CH_2$, $CH_2CH_2$, $CH{=}CH$, NR, or $CH{=}N$;

where G is $(CH_2)_{1\text{-}3}$, or $(CH_2)_{0\text{-}2}NR$;

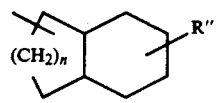

where n is 1-2,

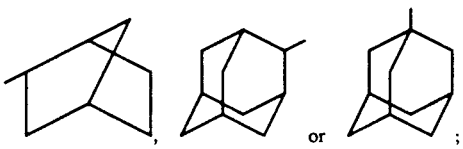

Z is

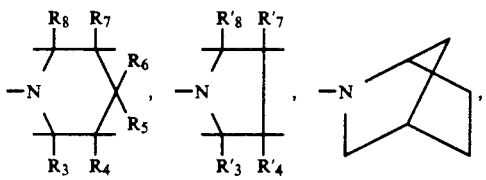

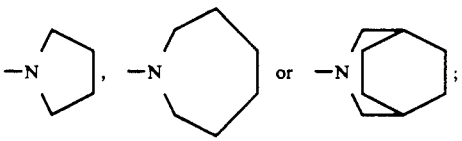

R, $R_1$, $R_2$ and R' are independently hydrogen or alkyl;

R" is cyclohexyl, cyclohexylmethyl, N-pyrrolidinyl, N-piperidinyl, phenyl, benzyl, phenethyl or styryl;

$R_3$, $R_4$, $R_5$, $R_6$, $R_7$ and $R_8$ are all hydrogen or $R_3$ and $R_4$ together, or $R_4$ and $R_5$ together form a phenylene group or —$(CH_2)_p$ where p is 4 or 5, or $R_3$ and $R_5$ together, or $R_3$ and $R_7$ together, or $R_3$ and $R_8$ together, are —$(CH_2)_q$— where q is 2 or 3, or $R_3$, $R_4$, $R_5$, $R_7$ and $R_8$ are all hydrogen and $R_6$ is cyclohexyl, cyclohexylmethyl, N-pyrrolidinyl, N-piperidinyl, phenyl, benzyl, phenethyl or styryl or $R_3$, $R_4$, $R_7$ and $R_8$ are all hydrogen and $R_5$ and $R_6$ together are —$(CH_2)_r$— where r is 4-6; or $R'_3$, $R'_4$, $R'_7$ and $R'_8$ are all hydrogen or $R'_3$ and $R'_4$ are hydrogen and $R'_7$ and $R'_8$ together form a phenylene group or —$(CH_2)_4$ or $R'_3$ and $R'_4$ together and $R'_7$ and $R'_8$ together form a phenylene group or —$(CH_2)_4$;

or a pharmaceutically acceptable salt thereof.

Preferred cyclic compounds contain a tertiary amino group capable of forming an ammonium ion at biological pH. This invention also provides novel bisphosphonate compounds and processes for their preparation.

DETAILED DESCRIPTION AND PREFERRED EMBODIMENTS

As employed above and throughout this disclosure, the following terms, unless otherwise indicated, shall be understood to have the following meanings:

"Alkyl", either alone or with an amino substituent defined herein, means a saturated aliphatic hydrocarbon, either branched- or straight-chained, having from one to twenty carbon atoms. Preferred alkyl is "loweralkyl" having about 1 to about 6 carbon atoms. Examples of loweralkyl include methyl, ethyl, n-propyl, isopropyl, butyl, sec-butyl, t-butyl, amyl and hexyl.

"Alkoxy" refers to an alkyl-O-group. Preferred loweralkoxy groups include methoxy, ethoxy, propoxy and butoxy.

Preferred compounds of this invention are described by Formula I where

A is hydrogen, hydroxy or alkoxy;
B is $(CR_1R_2)_m$ where m is 2;
D is Z, —NR—X or —NR—$(CH_2)_{1-2}$—Z;
X is

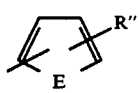

where E is CH=CH, NR, or CH=N;

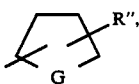

where G is $(CH_2)_{1-3}$, or $(CH_2)_{0-2}NR$;

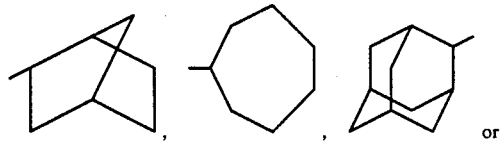

Z is

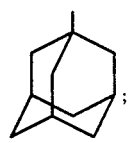, 

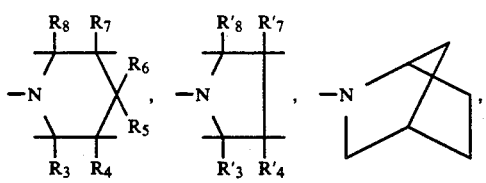

R, $R_1$, $R_2$ and R' are independently hydrogen or lower alkyl;
R" is hydrogen, cyclohexyl, phenyl or benzyl; and
$R_3$ and $R_4$, or $R_4$ and $R_5$ form a phenylene group or —$(CH_2)_p$ where p is 4, or $R_3$ and $R_5$, or $R_3$ and $R_7$, or $R_3$ and $R_8$, are —$(CH_2)_q$— where q is 2, or $R_3$, $R_4$, $R_5$, $R_6$, $R_7$ and $R_8$ are all hydrogen or $R_3$, $R_4$, $R_5$, $R_7$ and $R_8$ are all hydrogen and $R_6$ is cyclohexyl, cyclohexylmethyl, N-pyrrolidinyl, N-piperidinyl, phenyl, benzyl, phenethyl or styryl or $R_3$, $R_4$, $R_7$ and $R_8$ are all hydrogen and $R_5$ and $R_6$ together are —$(CH_2)_r$— where r is 5; and R'$_3$, R'$_4$, R'$_7$ and R'$_8$ are all hydrogen or R'$_3$ and R'$_4$ are hydrogen and R'$_7$ and R'$_8$ together form a phenylene group or —$(CH_2)_4$ or R'$_3$ and R'$_4$ together and R'$_7$ and R'$_8$ together form a phenylene group or —$(CH_2)_4$.

More preferred compounds include those compounds of Formula I where

A is hydroxy;
B is $CH_2CH_2$;
D is Z, —NH—X or —NH—$(CH_2)_{1-2}$—Z;
X is

where E is CH=CH, NR, or CH=N;

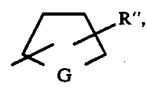

where G is $(CH_2)_{1-3}$, or $(CH_2)_{0-2}NR$;

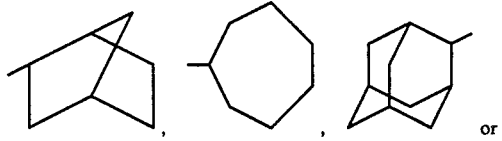

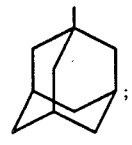

Z is

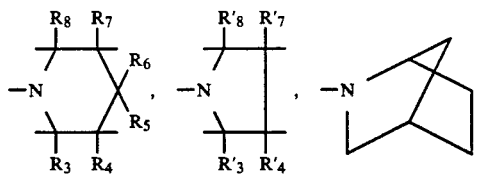

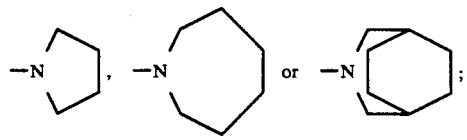

R, $R_1$, $R_2$ and R' are independently hydrogen or lower alkyl;
R" is hydrogen, cyclohexyl, phenyl or benzyl; and
$R_3$ and $R_4$, or $R_4$ and $R_5$ form a phenylene group or —$(CH_2)_p$ where p is 4, or $R_3$ and $R_5$, or $R_3$ and $R_7$, or $R_3$ and $R_8$, are —$(CH_2)_q$— where q is 2, or $R_3$, $R_4$, $R_5$, $R_6$, $R_7$ and $R_8$ are all hydrogen or $R_3$, $R_4$, $R_5$, $R_7$ and $R_8$ are all hydrogen and $R_6$ is cyclohexyl, cyclohexylmethyl, N-pyrrolidinyl, N-piperidinyl, phenyl, benzyl, phenethyl or styryl or R₃, R₄, R₇ and R₈ are all hydrogen and R₅ and R₆ together are —(CH₂)ᵣ— where r is 5; and R'₃, R'₄, R'₇ and R'₈ are all hydrogen or R'₃ and R'₄ are hydrogen and R'₇ and R'₈ together form a phenylene group or —(CH₂)₄ or R'₃ and R'₄ together and R'₇ and R'₈ together form a phenylene group or —(CH₂)₄.

Most preferred compounds include those compounds of Formula I where

A is hydroxy;
B is CH₂CH₂;
D is

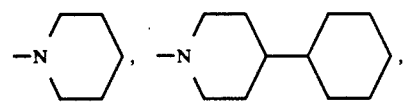

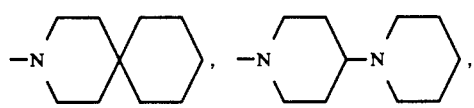

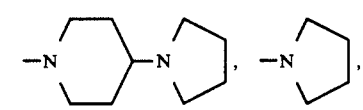

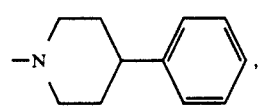

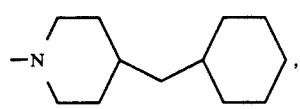

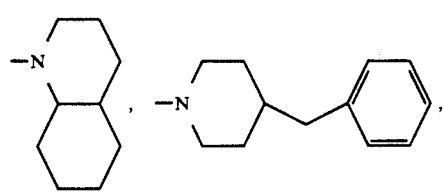

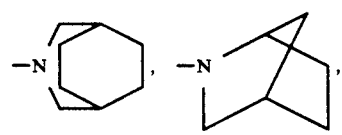

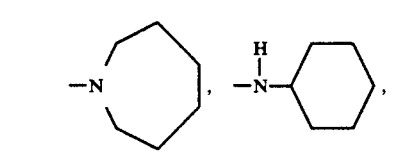

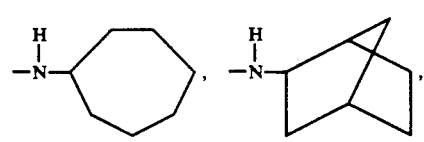

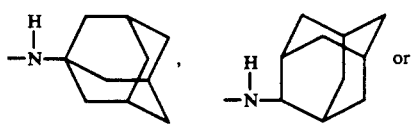

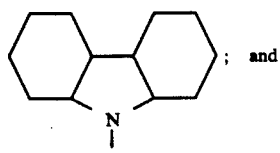

R' and R" are hydrogen.

A special embodiment of this invention is described where
D is Z, —NH—X or —NH—(CH₂)₁₋₂—Z;
Z is

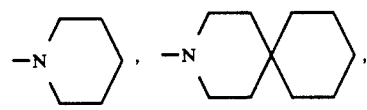

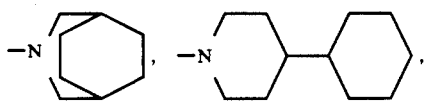

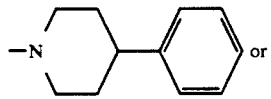

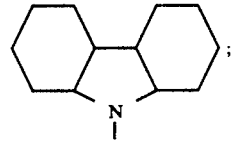

X is

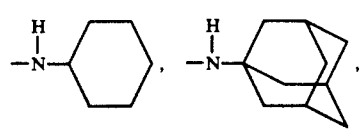

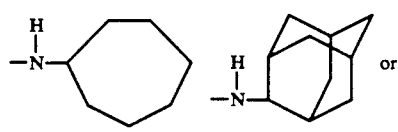

B is CH₂CH₂.

The compounds of this invention may be prepared from starting materials, which are either commercially available or described in the literature, by the following general procedures.

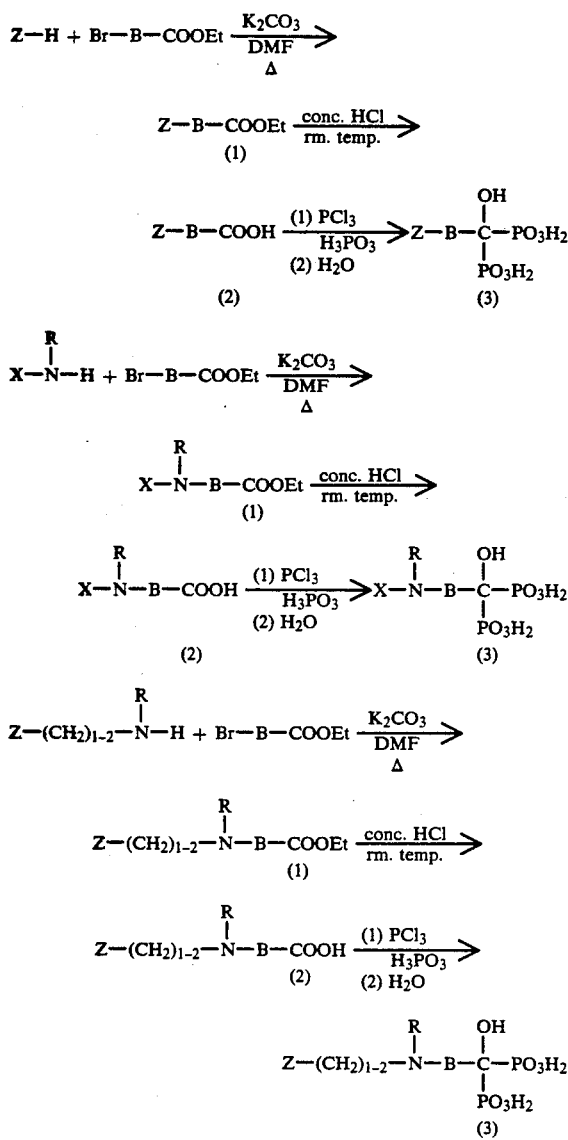

Condensation of a cyclic amine with a halo ester under basic conditions results in the formation of a cyclic amino ester (1). Hydrolysis to the acid (2) followed by treatment with phosphorous acid and phosphorous trichloride in an inert atmosphere results in the cyclic amino bisphosphonic acid (3).

Condensation of the cyclic amine with the halo ester is carried out in a polar solvent, preferably DMF, and in the presence of base such as $K_2CO_3$, $Na_2CO_3$, etc. This is accomplished at raised temperatures usually between about 40° to about 90° C. (preferably about 65° C.). The ester is then hydrolyzed with acid in the usual manner at about room temperature. Reaction of the carboxcyclic acid with phosphorous acid and phosphorous trichloride is carried out at raised temperatures between about 90° to about 150° C. (preferably about 120° C.) until the reaction is complete. This is usually carried out in an inert solvent, halobenzenes are preferred such as chlorobenzene.

When A is alkoxy the phosphonate esters are made in the normal manner from the esterification of the acid with an alcohol under acid conditions. When A is an amine the condensation may be carried out using the halo nitrile instead of the halo ester under ordinary conditions.

Representative compounds within the scope of the present invention are prepared by the following examples.

EXAMPLE 1

3-(1-adamantanamino)-1-hydroxypropane-1,1-bisphosphonic acid

Step A. ethyl 3-(1-adamantanamino)propionate

To a dry suspension of 1-adamantanamine (12 g, 1 eq.) and $K_2CO_3$ (11 g, 1 eq.) in DMF (60 mL) (under Ar) at 70° C. is added dropwise ethyl 3-bromopropionate (in DMF, 20 mL) over a 1.5 hour period. This is stirred for 24 hours at 70° and then overnight at room temperature. The reaction mixture is poured into 350 mL of ether: EtOAc (2:1), and the organic suspension washed with brine (3×40 mL). The aqueous layers are combined and extracted with EtOAc. The extract is dried over $Na_2SO_4$ and concentrated to give crude product. This material is chromatographed in 25% hexane/EtOAc over ~400 g S.G. (200–400 μm) to give ethyl 3-(1-adamantanamino)propionate which is used directly in the next step.

Step B. 3-(1-adamantanamino)propionic acid

Ethyl 3-(1-adamantanamino)propionate [(7.7 g)0.03 1 mol] is treated with 400 mL of aq. HCl for 2.5 hours. The mixture is then concentrated to give 8 g of 3-(1adamantanamino)propionic acid which is used directly in the next step.

Step C. 3-(1-adamantanamino)-1-hydroxypropane-1,1-bisphosphonic acid

To a stirred mixture of 3-(1adamantanamino)propionic acid [7.6 g(0.03 m)] and phosphoric acid [4.04 g (0.049 m)] in 20 mL. chlorobenzene at 120° C. is added $PCl_3$ [6.7 g/4.9 mL (0.049 m)] and the reaction mixture is heated at 120° C. for 6 hours, then cooled to room temperature overnight. Water is added and the mixture refluxed for about 2.5 hours then filtered through a thin pad of Celite. The chlorobenzene is extracted out with ether and the aqueous layer is evaporated to dryness to yield a colorless syrup. This crude product is treated with water and acetone added until a cloudy precipitate forms which crystallizes to yield 3-(1-adamantanamino)-1-hydroxypropane-1,1-bisphosphonic acid [m.p. 215° C.(dec)].

EXAMPLE 2

When the procedure of Example 1 is followed and 1-adamantanamine of Step A is replaced by the materials of Table I below, then the corresponding products are obtained. A representative list of compounds so prepared are shown in Table II below.

Table I 1-adamantanamine
2-adamantanamine
4-aminopyridine
1-methyl-4-aminopyridine
1-phenyl-4-aminopiperidine
1-benzyl-4-aminopiperidine
1-benzyl-3-aminopyrrolidine
1-ethyl-2-aminomethylpyrrole
aminomethylbenzene
aminomethylcyclohexane
aminoethylcyclohexane
aminopropylcyclohexane cyclohexylamine
1-aminoindane
1-aminomethylindane
2-(aminomethyl)-1-ethylpyrrolidine
2-(aminoethyl)-1-ethylpyrrolidine
2-norbornamine
cycloheptylamine
aminomethylcycloheptane
aminoethylcycloheptane
1-amino-1,2,3,4-tetrahydronaphthalene
1-aminomethyl-1,2,3,4-tetrahydronaphthalene
1-aminodecahydronaphalene
cyclohexylmethylamine

EXAMPLE 3

3-[N-(3-azabicyclo[3.2.2]nonane)]-1-hydroxypropane-1,1-bisphosphonic acid

Step A. ethyl 3-[N-(3-azabicyclo[3.2.2]nonane)]propionate

A mixture of 3-azabicyclo [3.2.2] nonane [5.2 g (0.04 m)], ethyl 3-bromopropionate [7.2 g (0.04 m], anhydrous $K_2CO_3$ [16.6 g (0.12 m)] in 40 mL DMF is stirred at 80° C. for ten hours. This is cooled, filtered, diluted with 200 mL $H_2O$ and extracted twice with EtOAc. The extract is then dried ($MgSO_4$) and evaporated to dryness to yield 3-[N-(3-azabicyclo[3.2.2]nonane)]-1-

TABLE II $$Q-CH_2CH_2-\underset{\underset{PO(OH)_2}{|}}{\overset{\overset{OH}{|}}{C}}-PO(OH)_2$$

| where Q is | m.p. °C. | elemental analysis calc'd | found |
|---|---|---|---|
| (1-aminoindanyl) | 160(dec) | | |
| (2-aminoadamantyl) | 198(dec) | | |
| (2-norbornyl amino) | 160(dec) | | |
| (cycloheptylmethyl ammonium · Na) | 220–260(dec) | | |
| (1-amino-1,2,3,4-tetrahydronaphthyl) | | C: 42.75<br>H: 5.79<br>N: 3.83 | 40.39<br>6.01<br>3.58 |
| (cyclohexylmethylamino) | 179–82(dec) | | |
| (1-benzyl-4-piperidylamino) | 175(dec) | | |
| (2,2,6,6-tetramethyl-4-piperidylamino) | | C: 32.22<br>H: 6.76<br>N: 6.27 | 33.09<br>7.13<br>6.68 | hydroxypropane-1,1-bisphosphonic acid which is used directly in the next step.

Step B. 3-[N-(3-azabicyclo[3.2.2]nonane)]propanoic acid

To ethyl 3-[N-(3-azabicyclo[3.2.2]nonane)]propionate [8 g (0.035 m)] in 40 mL ethanol is added 1N NaOH (40 mL) and stirred at room temperature for 10 hours. This reaction mixture is then evaporated to dryness, diluted with water and extracted with EtOAc. The aqueous layer is acidified to pH6 with conc. HCl, evaporated to dryness and the residue stirred with methanol. The resultant salt is filtered off and the alcohol solvent evaporated to dryness to yield 3-[N-(3-azabicyclo[3.2.2-]nonane)]propanoic acid which is used directly in the next step.

Step C. 3-[N-(3-azabicyclo[3.2.2]nonane)]-1-hydroxypropane-1,1-bisphosphonic acid To a stirred mixture of 3-[N-(3-azabicyclo[3.2.2-]nonane)]propanoic acid [5.8 g (0.03 m)] and phosphoric acid [3.6 g (0.044 m)] in 60 mL chlorobenzene at 120° C. is added PCl$_3$ [6.1 g (0.044 m)] and stirred at 120° C. for 14 hours. To this is added 100 mL H$_2$O and stirred at 120° C. for 2 hours. The reaction mixture is then suction filtered and the aqueous layer separated. The aqueous is washed with CHCl$_3$, treated with decolorizing charcoal, filtered and stripped to a small volume. The mixture is diluted with methanol and addition of acetone results in crystallization. The solid material is filtered and recrystalized from methanolacetone to yield 3-[N-(3-azabicyclo[3.2.2]nonane)]-1-hydroxypropane-1,1-bisphosphonic acid.

|   | Calc'd. | Found | Calc'd for free base + 1 mole H$_2$O |
|---|---------|-------|--------------------------------------|
| C | 34.79   | 36.09 | 36.57 |
| H | 6.37    | 6.50  | 6.98  |
| N | 3.69    | 2.86  | 3.88  |

EXAMPLE 4

When the procedure of Example 3 is followed and 3-azabicyclo[3.2.2]-nonane of Step A is replaced by the materials of Table III below, then the corresponding products are obtained. A representative list of compounds so prepared are shown in Table IV below.

Table III piperidine
piperazine
4-phenylpiperidine
1-phenylpiperazine
pyrrolidine
indoline
azacycloheptane
dodecahydrocarbazole
decahydroquinoline
3-azabicyclo[3.2.2]nonane
3-azaspiro[5.5]undecane
4-pyrrolidinopyridine
4-(pyrrolidin-1-yl)piperidine
1-(2-pyridyl)piperazine
4-(piperidin-1-yl)piperidine
1,3,3-trimethyl-6-azabicyclo[3.2.1]octane
1,2,3,4-tetrahydroquinoline
1,2,3,4-tetrahydroisoquinoline

TABLE IV

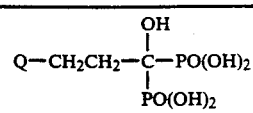

where Q is | m.p. °C. | elemental analysis calc'd | found |
|---|---|---|---|
| (4-phenylpiperidinyl) .HCl | 120-30 | | |
| (decahydroquinolinyl) .HCl | | C: 36.61<br>H: 6.66<br>N: 3.56 | 37.75<br>6.57<br>3.59 |
| (3-azabicyclo[3.2.2]nonanyl) | | C: 38.49<br>H: 6.75<br>N: 4.08 | 36.09<br>6.50<br>2.86 |
| (piperidinyl) | 205-7 | | |
| (azacycloheptanyl) .Na | 238-42 (dec) | | |
| (1,3,3-trimethyl-6-azabicyclo[3.2.1]octanyl) | 125-35 (dec) | | |
| (3-azaspiro[5.5]undecanyl) | | C: 42.05<br>H: 7.33<br>N: 3.77 | 40.85<br>6.98<br>3.64 |
| (4-pyrrolidinopiperidinyl) | | C: 35.29<br>H: 6.65<br>N: 6.85 | 33.97<br>6.24<br>6.50 |
| (4-piperidinopiperidinyl) | | C: 36.93<br>H: 6.91<br>N: 6.63 | 37.47<br>7.03<br>6.92 |
| (dodecahydrocarbazolyl) | | C: 45.34<br>H: 7.36<br>N: 3.53 | 43.10<br>7.37<br>3.34 |

EXAMPLE 5

When ethyl 3-bromopropionate in Examples 1 and 3 is replaced with ethyl 3-chloropropenoate, 4- bromobutenoate or 3-bromobutenoate then the corresponding compound is prepared.

Various tests in animal tissue have been carried out to show the ability of the compounds within the scope of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene synthetase and hence are believed to be useful in the treatment of cholesterol-related disorders.

Squalene Synthetase Inhibition Assay

The squalene synthetase assay used is a modification of the procedures described by Popjak (1969) and Poulter et al. (1989):

Popjak, G. Enzymes of sterol biosynthesis in liver and intermediates of sterol biosynthesis. Meth. Enzymol. 15: 393–454, 1969.

Poulter, C. D., Capson, T. L., Thompson, M. D. and Bard R. S. Squalene synthetase. Inhibition by ammonium analogues of carbocationic intermediates in the conversion of presqualene diphosphate to squalene. J. Am. Chem. Soc. 111: 3734–3739, 1989.

I. Animal Source and Tissue Preparation

Four male Sprague-Dawley rats weighing 100–120 gms are fed a low cholesterol rodent diet (#5012) obtained from Purina Mills, Inc. in Richmond, Ind.; and housed under reverse-light. Water is given ad lib. Rats are lightly anesthetized with ether and then decapitated. Livers are removed and enzymes are separated by the method described below.

II. Materials

Chemicals:

All Chemicals are "A.C.S." in purity or better unless noted;

AquaSol®-2 scintillation fluid (NEF-952) (Du Pont/NEN Research Products, Boston, Mass.);

Anhydrous $MgCl_2$ (M-8266), $\beta$-NADPH tetrasodium salt, reduced form (N-1630), Bovine serum albumin (A-6003), Cholesterol (C-8503);

Squalene (S-3626), (Sigma Chemical Co., St. Louis, Mo.);

Bio-Rad protein assay dye concentrate (Bio-Rad Laboratories, Richmond, Calif.);

Denatured ethanol, DMSO, HCl (1N), KOH, methanol, NaOH (0.1N, 1N), petroleum ether (M-280 grade), potassium phosphate dibasic, 2-propanol (Fisher Scientific, Pittsburgh, Pa.);

Zero grade nitrogen gas mixture (certified analysis) (Woodland Oxygen & Supply Co., Philadelphia, Pa.).

Radiochemicals:

[1-$^3$H(N)]-FPP, triammonium salt (NET-1042), (Du Pont/NEN, Boston, Mass.);

[4,8,12,13,17,21-$^3$H]-Squalene (NET-645) (Du Pont/NEN);

Non-radiolabeled FPP is prepared in-house. The solid FPP is aliquoted and stored at −80° C. FPP is dissolved in 70% ethanol/30% 0.25M $NH_4HCO_3$ at the concentration of 10 mM and the solution is aliquoted (200 $\mu$l each) and stored at −80° C.

III. Preparation of Assay Substances

A) Test Solutions:

Test solutions are prepared fresh in 100% DMSO or $dH_2O$. Subsequent dilutions are made in the same solvent. Compounds are tested initially at 1 or 10 $\mu$M (final concentrations).

B) Assay Buffer:

Potassium phosphate (50 mM, 8.71 g/l) pH 7.5 stock buffer is prepared and stored at 4° C. until use. Anhydrous $MgCl_2$ is added to the phosphate buffer on the day of assay for a final concentration of 10 mM (95 mg/100 ml). The buffer is flushed with $N_2$ before use.

C) Substrate:

Non-radiolabeled FPP is diluted to 50 $\mu$M (100 $\mu$l 10 mM cold FPP + 19.9 ml phosphate buffer). Then, 14 $\mu$l (20×10$^6$ dpm) of $^3$H-FPP (0.5 mCi/ml, 0.011 mg/ml) is added. 200 $\mu$l of this mixture is added per assay tube for a final reaction concentration of 10 $\mu$M FPP (~200,000 dpm/assay tube).

D) $\beta$-NADPH Solution:

37.5 mg of $\beta$-NADPH is added to 9 ml assay buffer for a 5 mM concentration of $\beta$-NADPH. The mixture is vortexed and 100 $\mu$l of this solution is added to each tube for a final assay concentration of 0.5 mM $\beta$-NADPH.

E) KOH in Ethanol:

75 gm of KOH is dissolved in 500 ml of denatured ethanol for a 15% solution and stored at 0° C. until use. 1 ml of this solution is added per tube to terminate the reaction.

IV. Experimental Procedure

A) Enzyme Preparation:

Immediately following decapitation, livers are removed one at a time from four rats. The livers are combined and weighed in a tared beaker. Assay buffer is added equal to three times the liver weight. The liver is first homogenized with a blender for thirty seconds, and then by a motor driven teflon pestle at a speed of 2.5. During homogenization, the liver is kept on ice. When the liver is fully homogenized, the homogenate is centrifuged at 10,000 g for 30 min at 4° C. in 50 ml capacity centrifuge tubes. The mitochondrial pellet is discarded and the supernatant is filtered through a layer of gauze moistened with a little buffer. This supernatant is recentrifuged at 105,000 g for one hour at 0° C. in an ultracentrifuge in 25 ml capacity ultracentrifuge tubes.

Following centrifugation, the supernatant is removed and discarded. The sediment pellet consists of 2 layers: a transparent inner layer of glycogen, surrounded by an opaque brown layer of microsomes. The brown outer microsomal layer is carefully removed with a spatula and placed in a beaker on ice. Assay buffer is added in an amount equal to one half the original homogenate volume, and this mixture is poured into ultracentrifuge tubes. These tubes are recentrifuged at 105,000 g for 1 hour at 4° C.

After this centrifugation is complete, the supernatant is again removed and discarded. Fresh assay buffer is added to the combined pellets to achieve a volume equal to one tenth of the original homogenate volume. The microsomal fraction is then rehomogenized on a motor driven teflon pestle at a speed of 2.5 to partially solubilize and make a uniform suspension of the microsomes. The enzyme (~20 ml, ~40 mg protein/ml) is aliquoted (200 $\mu$l) into eppendorf plastic tubes, capped and stored at −80° C. until use.

B) Assay Procedure

To begin the assay, 20 $\mu$l of the compound of this invention or vehicle solution is added to each 16×150 screw-cap culture tube on ice. Then 580 $\mu$l of $N_2$ flushed assay buffer is pipetted into each tube. 100 $\mu$l of cofactor is next added to each tube, followed by 100 $\mu$l of a dilution of microsomal enzyme (approximately 80 ug protein). The tubes are preincubated for 10 minutes at 37° C., and 200 μl of the ³H-FPP (200,000 dpm, 10 μM final conc.) is added to each tube at two second intervals. The tubes are then incubated for exactly 10 minutes, shaking at 150 oscillations per minute. After the 10 minute incubation, the reaction is stopped by the addition of 1 ml of 15% KOH in ethanol, and the tubes are incubated for 30 minutes in a 65° C. water bath for saponification of lipids and solubilization of proteins. The tubes are cooled on ice for five minutes. The samples are next extracted with 5 ml of petroleum ether by shaking for 10 minutes at low speed on a metabolic shaker. Each lower aqueous layer is frozen in a dry ice/alcohol bath (2-propanol/methanol, 1:1), and each organic layer is poured into another set of 16×150 screw-top culture tubes containing 2 ml of deionized water. Each ether layer is washed by vortexing each tube for 5 seconds. The aqueous layers are again frozen in the dry ice/alcohol bath, and the ether is poured into scintillation vials. 10 ml of AquaSol ® is next added to each vial, and the vials are counted for 5 minutes in a scintillation counter. Percent inhibitions are calculated from the counts obtained.

V. Statistical Consideration

The samples are counted as dpm using a Beckman Scintillation counter (Model LS-9000). Percent inhibition is calculated using a Lotus 1-2-3 program. The IC$_{50}$ values are calculated using a linear regression program of Tallarida and Murray (1987). Tallarida, R. J. and Murray, R. B. Manual of pharmacologic calculations with computer programs. Springer-Verlag, 1987.

The following table demonstrates the results of the foregoing assay when compounds of the present invention are subjected to this assay.

$$Q-CH_2CH_2-\underset{PO(OH)_2}{\underset{|}{\overset{OH}{\overset{|}{C}}}}-PO(OH)_2$$

| where Q is | SQ SYN IC$_{50}$(μM) |
|---|---|
| 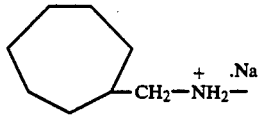 | 0.06 |
| 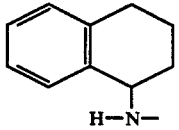 | 0.44 |
| 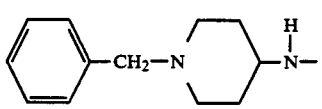 | 0.60 |

-continued $$Q-CH_2CH_2-\underset{PO(OH)_2}{\underset{|}{\overset{OH}{\overset{|}{C}}}}-PO(OH)_2$$

| where Q is | SQ SYN IC$_{50}$(μM) |
|---|---|
| 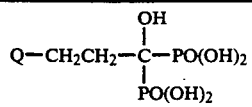 | 1.46 |
| 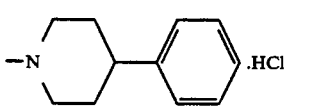 | 0.13 |
| 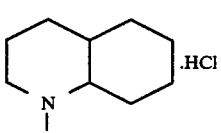 | 2.30 |
|  | 0.37 |
|  | 0.019 |
| 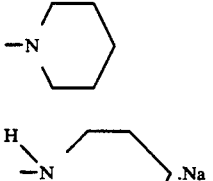 | 0.016 |
|  | 0.72 |
| 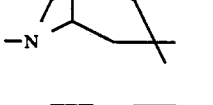 | 0.13 |
| 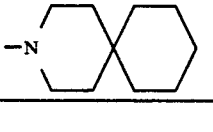 | 5.06 |
|  | 0.39 |

In view of the results obtained by the foregoing assay procedure, compounds within the scope of Formula I inhibit squalene synthetase enzyme activity and are useful as hypocholesterolemic or hypolipidemic agents by virtue of their ability to inhibit the biosynthesis of cholesterol. Accordingly, the present invention utilizes at least one of such hypocholesteremically effective compounds in combination with pharmaceutically acceptable carriers in the form of pharmaceutical compositions for administration to a patient exhibiting abnormally high serum cholesterol levels to lower such levels and maintain a pharmacologically acceptable lowered cholesterol level.

In accordance with the biosynthetic pathway theory discussed above, treatment with a combination of an HMG-CoA reductase inhibitor and a squalene synthetase inhibitor would most closely resemble the physiological conditions of cholesterol homeostasis. A squalene synthetase inhibitor could keep cellular concentrations of farnesyl pyrophosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used. Accordingly, the present invention also comprises the administration of pharmaceutically effective amounts of both any therapeutically effective HMG-CoA reductase inhibitor, known in the literature, and a squalene synthetase inhibitor within the scope of the present invention.

The compounds of the present invention can be administered to a mammalian host in a variety of forms adapted to the chosen route of administration, i.e., orally, or parentally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, when an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and about 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 100 mg/kg/dy, and preferably from about 10 mg to about 1000 mg day, or from about 0.1 mg to about 50 mg/kg of body weight per day and preferably from about 0.1 to about 20 mg/kg of body weight per day and may be administered in several different dosage units. Higher dosages on the order of about 2× to about 4× are required for oral administration.

We claim:

1. A method of lowering serum cholesterol or maintaining lowered serum cholesterol in a patient requiring such treatment which comprises administering to such patient a squalene synthetase inhibitor effective amount of a compound selected from the group consisting of:

3-[3-azabicyclo[3.2.2]non-3-yl]-1-hydroxypropylidene-1,1-bisphosphonic acid, which is

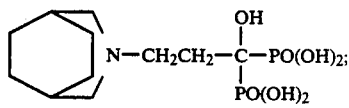

3-[adamant-2-ylamino]-1-hydroxypropylidene-1,1-bisphosphonic acid, which is

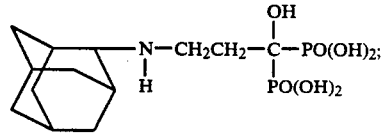

or
3-[norborn-2-ylamino]-1-hydroxypropylidene-1,1-bisphosphonic acid, which is

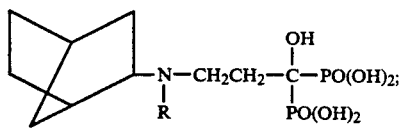

or a pharmaceutically acceptable salt thereof.

2. A method according to claim 1 where the patient is in need of a hypocholesterolemic or hypolipidemic agent.

3. A pharmaceutical composition comprising a squalene synthetase inhibitor effective amount of a compound described by the formula of claim 1 in admixture with a pharmaceutical carrier.

4. A method of lowering serum cholesterol or maintaining lowered serum cholesterol in a patient requiring such treatment which comprises administering to such patient a squalene synthetase inhibitor effective amount of a compound selected from the group consisting of:

3-[1-azacyclohept-1-yl]-1-hydroxypropylidene-1,1-bisphosphonic acid, which is

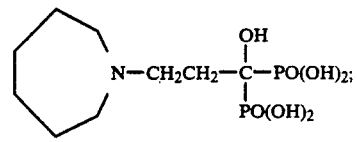

3-[piperidin-1-yl]-1-hydroxypropylidene-1,1-bisphosphonic acid, which is

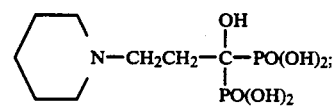

3-[N-decahydroquinolinyl]-1-hydroxypropylidene-1,1-bisphosphonic acid, which is

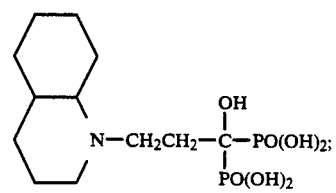

or
3-[4-phenylpiperidin-1-yl]-1-hydroxypropylidene-1,1-bisphosphonic acid, which is

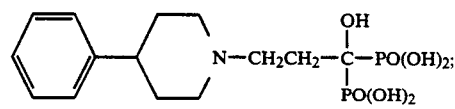

or a pharmaceutically acceptable salt thereof.

5. A method according to claim 4 where the patient is in need of a hypocholesterolemic or hypolipidemic agent.

6. A pharmaceutical composition comprising a squalene synthetase inhibitor effective amount of a compound described by the formula of claim 4 in admixture with a pharmaceutical carrier.

7. A method of lowering serum cholesterol or maintaining lowered serum cholesterol in a patient requiring such treatment which comprises administering to such patient a squalene synthetase inhibitor effective amount of a compound selected from the group consisting of:

3-[1-indanylamino]-1-hydroxypropylidene-1,1-bisphosphonic acid, which is

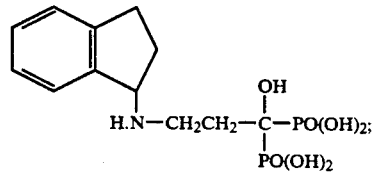

or
3-[1,2,3,4-tetrahydronaphth-1-ylamino]-1-hydroxypropylidine-1,1-bisphosphonic acid, which is

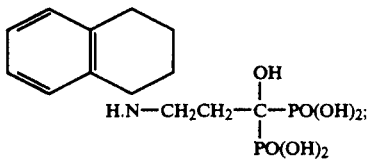
or a pharmaceutically acceptable salt thereof.
8. A method according to claim 7 where the patient is in need of a hypocholesterolemic or hypolipidemic agent.
9. A pharmaceutical composition comprising a squalene synthetase inhibitor effective amount of a compound described by the formula of claim 7 in admixture with a pharmaceutical carrier.
* * * * *